United States Patent [19]

Rees

[11] Patent Number: 4,869,531
[45] Date of Patent: Sep. 26, 1989

[54] APPARATUS AND METHOD FOR DOCUMENTING PHYSICAL EXAMINATIONS

[76] Inventor: Michael K. Rees, 115 Colburn Crescent, Brookline, Mass. 02146

[21] Appl. No.: 176,430

[22] Filed: Apr. 1, 1988

[51] Int. Cl.$^4$ .................. B42D 15/00; B42F 5/00; A47F 3/14; G09B 23/28
[52] U.S. Cl. ................................ 283/67; 283/81; 211/128; 434/272
[58] Field of Search .................... 283/81, 900, 67; 150/132; 221/110, 111, 112; 434/261, 262, 263, 264, 269, 270, 272; 211/55, 128, 206

[56] References Cited

U.S. PATENT DOCUMENTS

| | | | |
|---|---|---|---|
| 340,270 | 4/1886 | Yaggy | 434/269 |
| 421,833 | 2/1890 | Henckel | 434/269 |
| 2,139,009 | 12/1938 | Ford et al. | 211/128 |
| 3,777,795 | 12/1973 | Graetz | 150/147 |
| 4,029,341 | 6/1977 | Neill et al. | 283/900 |
| 4,105,057 | 8/1978 | Baumann et al. | 150/132 |
| 4,156,539 | 5/1979 | Davidson et al. | 283/81 |
| 4,323,351 | 4/1982 | Goldsmith | 434/272 |
| 4,428,733 | 1/1984 | Kumar-Miser | 283/900 |
| 4,464,122 | 8/1984 | Fuller et al. | 283/900 |
| 4,716,948 | 1/1988 | Bressette | 150/132 |

FOREIGN PATENT DOCUMENTS

| | | | |
|---|---|---|---|
| 2250281 | 4/1975 | France | 283/900 |
| 2458861 | 1/1981 | France | 283/900 |

Primary Examiner—Frank T. Yost
Assistant Examiner—Paul M. Heyrana, Sr.
Attorney, Agent, or Firm—Bromberg & Sunstein

[57] ABSTRACT

Apparatus and method for documenting the findings of a physical examination. A group of pre-printed stickers are provided having an anatomical designation (either graphic or text) on the front surface of the sticker and an adhesive and peel-off back sheet on the rear of the sticker. The stickers are positioned in a dispenser with at least a portion of the anatomical designation visible from the sticker to facilitate selection of the desired stickers during the examination. The physician or patient can mark directly on the sticker to indicate the location, size and shape of any abnormality, and the back sheet is then removed and the sticker attached directly onto the patient's progress report. The system is an inexpensive method for fully documenting all findings from an examination in a minimum period of time and provides a permanent record which facilitates retrieval of the desired information from the report and minimizes the volume of patient records. The dispenser can be either a desk-top dispenser or a portable wallet.

17 Claims, 6 Drawing Sheets

99

| | |
|---|---|
| GENERAL: | The patient appears well (and approximately of stated age). |
| VITAL SIGNS: | Weight_____ Height_____ Blood Pressure_____<br>Temperature_____ Pulse_____ Respiration_____ |
| EYES: | The lids are normal. The pupils are equal. The conjunctivae reveal no evidence of infection. The sclerae are normal. The fundi reveal sharp discs and the vessels have good pulsations. No hemmorhages or exudates are present. The intraocular pressure is normal. |
| EARS: | The canals are not obstructed by wax. The tympanic membranes reveal no evidence of fluid or infection. |
| NOSE: | The nose is free of any evidence of infection or obstruction. |
| OROPHARYNX: | The teeth are in good repair. The gums appear healthy. The tonsils are normal for age and not infected. There is no mucosal exudate. |
| NECK: | The thyroid is not enlarged, and there is no nodule present. There are no abnormal nodes. The carotids are full and there are no bruits. |
| LUNGS: | The lungs are clear. There are no wheezes, rales, or rhonchi. There is no dullness to percussion. |
| HEART: | The heart has a normal rhythm. There are no murmurs. No S3 or S4 sound is present. |
| BREASTS: | The breasts appear symmetrical. Their consistency is smooth (lumpy, firm). The nipples are not retracted and there is no discharge. No mass is present. |
| ABDOMEN: | The abdomen is soft; neither the liver nor the spleen is enlarged. There is no mass or hernia present. There is no tenderness. |
| FEMALE GENITALIA: | The labia are normal. The vagina is normal. The cervix reveals no erosion. There is no discharge. The uterus is neither enlarged or irregular. A pap was done. |
| MALE GENITALIA: | The testes reveal no mass. The penis is normal. There is no discharge. The prostrate is soft, normal in size, and no nodule is present. |
| RECTAL: | No mass is present. No hemmorhoids are present. The stool is guiac negative (positive). |
| SKIN: | No rash is present. There are no scars. No suspicious or benign lesions are present. |
| BACK: | The back is flexible. There is no scoliosis. There is no tenderness. |
| NEURO: | The cranial nerves are normal. Sensory exam is normal. Reflexes are active and equal throughout. Muscle strength is adequate and symmetrical. The cerebellum tests normally. |
| EXTREMITIES: | The joints are normal. Pulses are equal and active throughout. There is no clubbing. There is no edema. No vericose veins are present. |

26

FEMALE PHYSICAL EXAM Chart-II™ 3002

Fig. 6

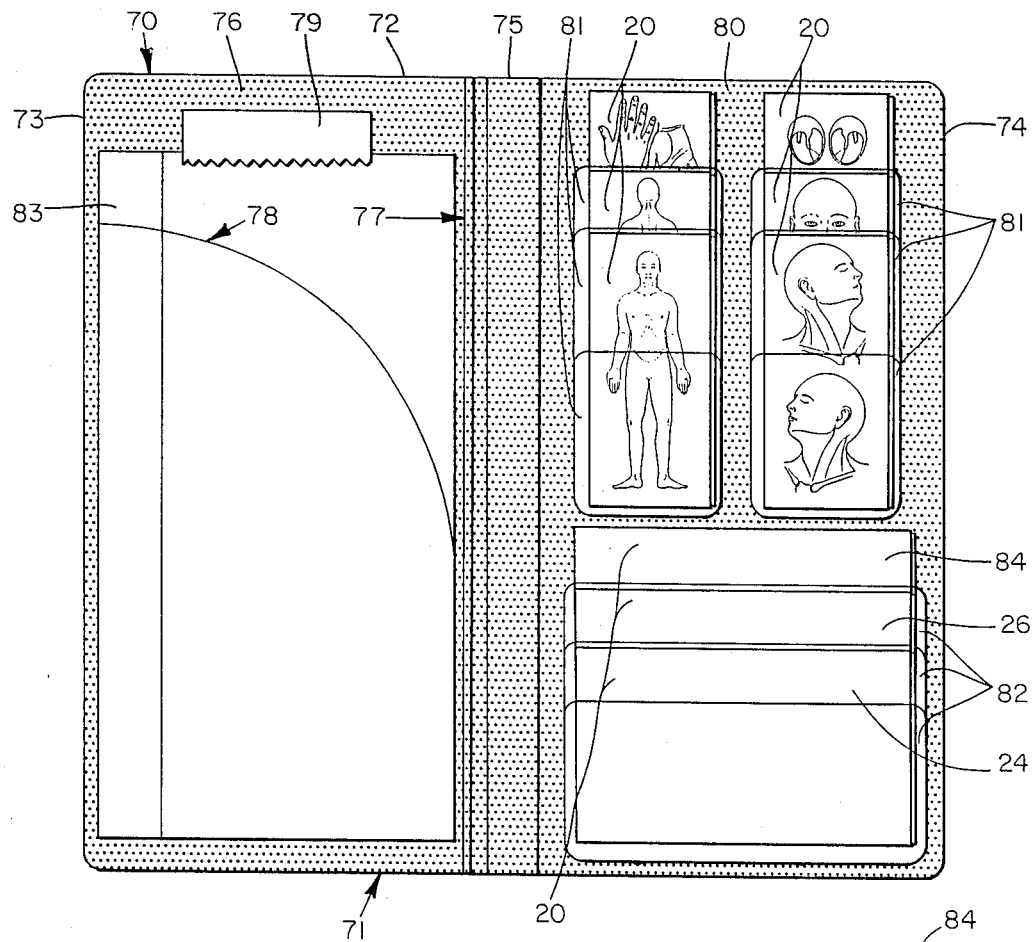
Fig. 7
Fig. 8
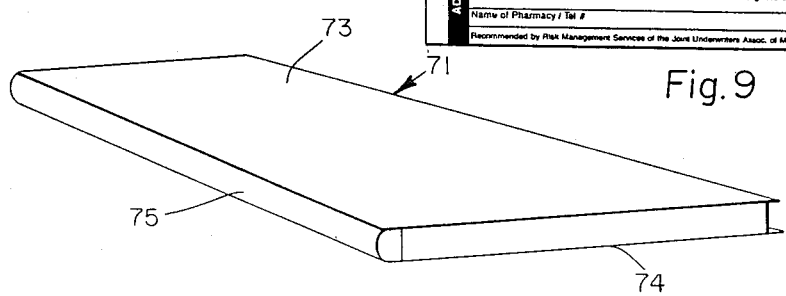
Fig. 9

Front

| Name | | | | | | | | | | | | | | | Location | | | | | | | | | | | | | | | | |
|---|---|---|---|---|---|---|---|---|---|---|---|---|---|---|---|---|---|---|---|---|---|---|---|---|---|---|---|---|---|---|---|
| Consultation<br>Hospital Visit | | | | Nursing Home<br>House Call | | | | | | | | | | B (Brief)<br>I (Intermediate) | | | | | | E (Extended)<br>C (Comprehensive) | | | | | | | | | | | |
| Month | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| | | | | | | | | | | | | | | | | | | | | | | | | | | | | | | | |
| | | | | | | | | | | | | | | | | | | | | | | | | | | | | | | | |

Notes:

Diagnoses:

Rear

| Referring Physician | |
|---|---|
| Date of Birth | S.S.# |
| Address | |
| | Tel.# |
| Insurance Data: Policy | |
| Group# | Policy# |
| Subscriber | Relationship |
| Address (If Diff.) | |
| Employer | |

Fig. 10

APPARATUS AND METHOD FOR DOCUMENTING PHYSICAL EXAMINATIONS

BACKGROUND OF THE INVENTION

This invention relates to an apparatus and method for documenting the findings of a physical examination.

The physician today confronts the following problems in his/her medical practice: the continually rising cost of overhead; the persistently shrinking patient base; the ever downward pressure on fees; the increasing risk of malpractice exposure; and the increasing need for better record keeping. Physicians must compensate for the increased cost of doing business by introducing practice efficiencies and by becoming more productive.

Traditionally, twenty minutes has been designated as the time required for a routine clinical encounter. However, because of economic pressures, many physicians are now expected to complete an encounter within nine to twelve minutes. To accomplish this without producing either patient dissatisfaction or error, the physician must have a method of both rapidly recording as well as rapidly retrieving patient information.

While economic pressures are reducing the time available for making a patient record, there is an ever increasing demand for better records. Accurate, complete, and easy-to read records become very important in a group practice where more than one physician may see a patient, and are required for a Medicare audit or an investigation of a malpractice claim.

In today's medical malpractice climate, it is especially important to keep accurate records. In many cases the courts have found that, "If the physician didn't document it, he didn't do it." The inability to document what was done is one of the most frequent reasons that malpractice suits are lost. Malpractice suits usually arise years after the encounter, and it is impossible to predict which encounter or problem may trigger a suit.

Some physicians choose to dictate a patient report during or after the examination. However, at an average transcription cost of about $2.30 per report, this is a costly procedure. Furthermore, if there is any ambiguity in the dictated message, often there is no other record to clarify the ambiguity.

Other physicians use pre-printed forms to save time and reduce error. A pre-printed form may take the physician through a standard exam in a logical order and allow normal findings to be checked off. However, it is difficult to use pre-printed forms for routine office visits because of the unpredictable nature of any encounter. Further, to use only pre printed forms would rapidly fill up a chart with separate pieces of paper. Filing space is usually at a premium, and fat records with little information waste valuable space.

Physicians may also purchase rolls of stick-on labels suitable for use on insurance and collection files, laboratory reports and samples, and on patient records. However, the scope to these labels is too limited to provide any measurable assistance in a routine office visit where a wide range of medical problems may be encountered.

It is an object of this invention to provide an apparatus and method for documenting the findings of a physical examination.

Another object is to provide a system for accurately and completely documenting a physical examination in less time and at a reduced cost.

Another object is to provide a system for accurately and completely documenting a physical examination without generating voluminous patient records.

Yet another object of the invention is to provide a system wherein anatomical drawings are provided to speed the description of abnormal/positive findings.

A further object of the invention is to provide a system wherein a permanent record of a matter discussed at the examination is made by the patient.

A further object of the invention is to provide a system for generating a patient report that is legible and easy to read.

A still further object of the invention is to provide a system for generating a patient report wherein information is recorded at predictable locations and thus rapidly retrieved.

Another object of the invention is to provide a system wherein normal/negative findings are rapidly and completely documented using a check-mark system.

SUMMARY OF THE INVENTION

This invention concerns a new way to rapidly and accurately document the findings of a physical examination. It is designed to save the physician time and money while at the same time enhancing accuracy and reducing malpractice risks. The apparatus includes a dispenser which contains a pre-printed examination form which is broken down into separate components. The components are pre-printed cards having an anatomical designation on one surface and an adhesive with a peel-off backing sheet on the other surface. The physician creates his/her own individualized progress notes while he/she examines the patient. Preferably, part of the record is made by the patient himself. It generally takes no more than 30 to 90 seconds to record the findings of even a complete physical examination, and at a cost of between 5 to 25¢. All steps can be completed while the physician is with the patient. At the termination of the visit, the physician's notes are complete, and the chart is ready to be filed. If the physician chooses to dictate his/her notes, the apparatus of this invention ensures a permanent record that facilitates dictation and serves as a back-up should a problem occur with the tape or should transcription be delayed. The dispenser may either be a desk-top dispenser or a portable wallet.

BRIEF DESCRIPTION OF THE DRAWINGS

FIG. 6 is a top plan view comparing a prior art narrative left with a sticker of this invention on the right.

FIG. 7 is a top plan view of a portable record keeping system of this invention, showing the interior of the w which forms part of the system.

FIG. 8 is a side perspective view of the wallet in a closed position.

FIG. 9 is a top plan view of an encounter form sticker used in this invention.

FIG. 10 is a top plan view of the front and rear surfaces of a visitation slip used in this invention.

DETAILED DESCRIPTION OF THE PREFERRED EMBODIMENTS

Figure 1:
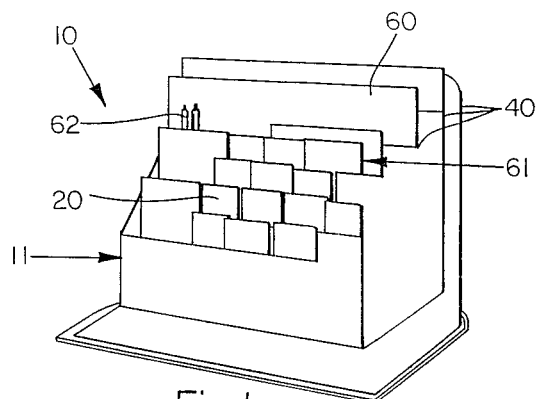
FIG. 1 is a perspective view of the physical examination kit of this invention.

This invention concerns a system of pre-printed self-adhering stickers that allows physicians to instantaneously prepare a pre-printed progress note. The system does not require the physician to change either his or her usual method of maintaining the patient record or chart or the chart folder. The system includes a variety of stickers having an anatomical designation (i.e., either a graphical or textual description of a body part and/or symptom) on one surface and an adhesive on the other surface, and a unique dispenser. The preprinted stickers allow the physician to check off normal findings and to denote the size, location and shape of abnormal findings or symptoms with a minimal of additional narrative. The stickers allow the physician to instantaneously document a normal condition. The recording of abnormal findings is highly accurate and entirely reproducible.

The examination kit 10 (FIG. 1) sits conveniently on the physician's examination room desk. The kit includes a base 50 (FIG. 4), a dispenser 11 (FIG. 3) for holding stickers 20 disposed in a front cavity 52 of the base, and three vertical sheet dividers 40 (FIG. 4) disposed in spaced-apart slots at the rear of the base. Blank progress report sheets 60 and lab requisition slips are held between the dividers 40.

Traditionally, examination room desks are small. The base holds the progress reports 60 and stickers 20 conveniently and occupies a minimum amount of space. Alternatively, the dispenser 11, which occupies only 3.5×4×8 inches, yet holds more than 1100 stickers, can be used alone.

The dispenser 11 (FIGS. 2–3) is constructed so that an identifiable portion of all stickers 20 are in view. The dispenser also holds the physician's prescription pad 61, writing instruments 62 (pens, pencils, crayons, markers), and perhaps other items of routine use to the physician, such as lab requisition slips. By holding prescription blanks, the dispenser remains useful to the physician in the event a particular clinical encounter does not require one of the pieces of information it contains.

Figure 2:
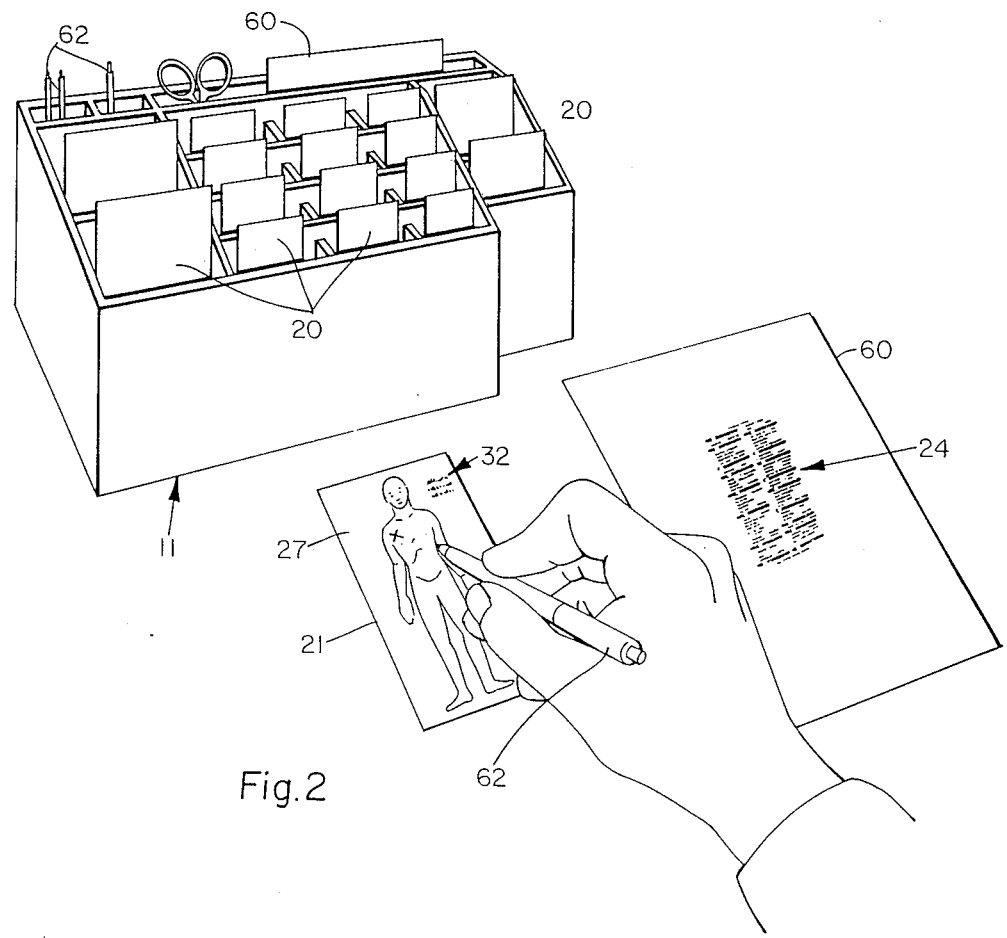
FIG. 2 is a schematic diagram of a physician using the physical examination kit of this invention to record the findings from the examination.
Figure 3:
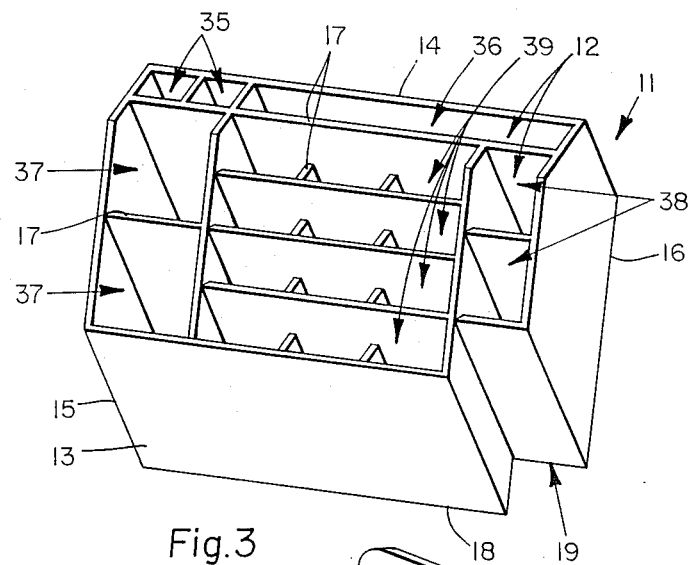
FIG. 3 is a top perspective view of the dispenser.

As shown in FIGS. 1–3, the dispenser 11 is a molded plastic body consisting of opposed vertical front and rear walls 13, 14 and opposed vertical sidewalls 15, 16. The bottom of dispenser 11 is closed by wall 18. A cut-out portion 19 is provided in the front right corner. Interior dividing walls 17 are provided for separating the dispenser into a number of compartments 12. Two narrow compartments 35 are provided in the rear left corner for holding writing instruments 62. An elongated compartment 36 is provided along the rear wall for holding a prescription pad 61. Pairs of compartments on the left and right 37, 38 and four sub-divided compartments 39 in the center are provided for holding the stickers 20. The compartments for holding the stickers form a tiered array which allows at least a portion of the front sticker in each compartment to be visually identified while held in the dispenser. A stack of individual stickers in face to-face relationship are disposed in each compartment. Optionally, cut-out portions (not shown) can be provided in the front wall of a compartment to further facilitate identification of the stickers in the compartment. Optionally, the compartments 35 for holding writing instruments can be positioned on the right side, which may be more convenient for right handed users. The invention is nor limited to the specific number or arrangement of compartments shown, nor to their dimensions.

Figure 5:
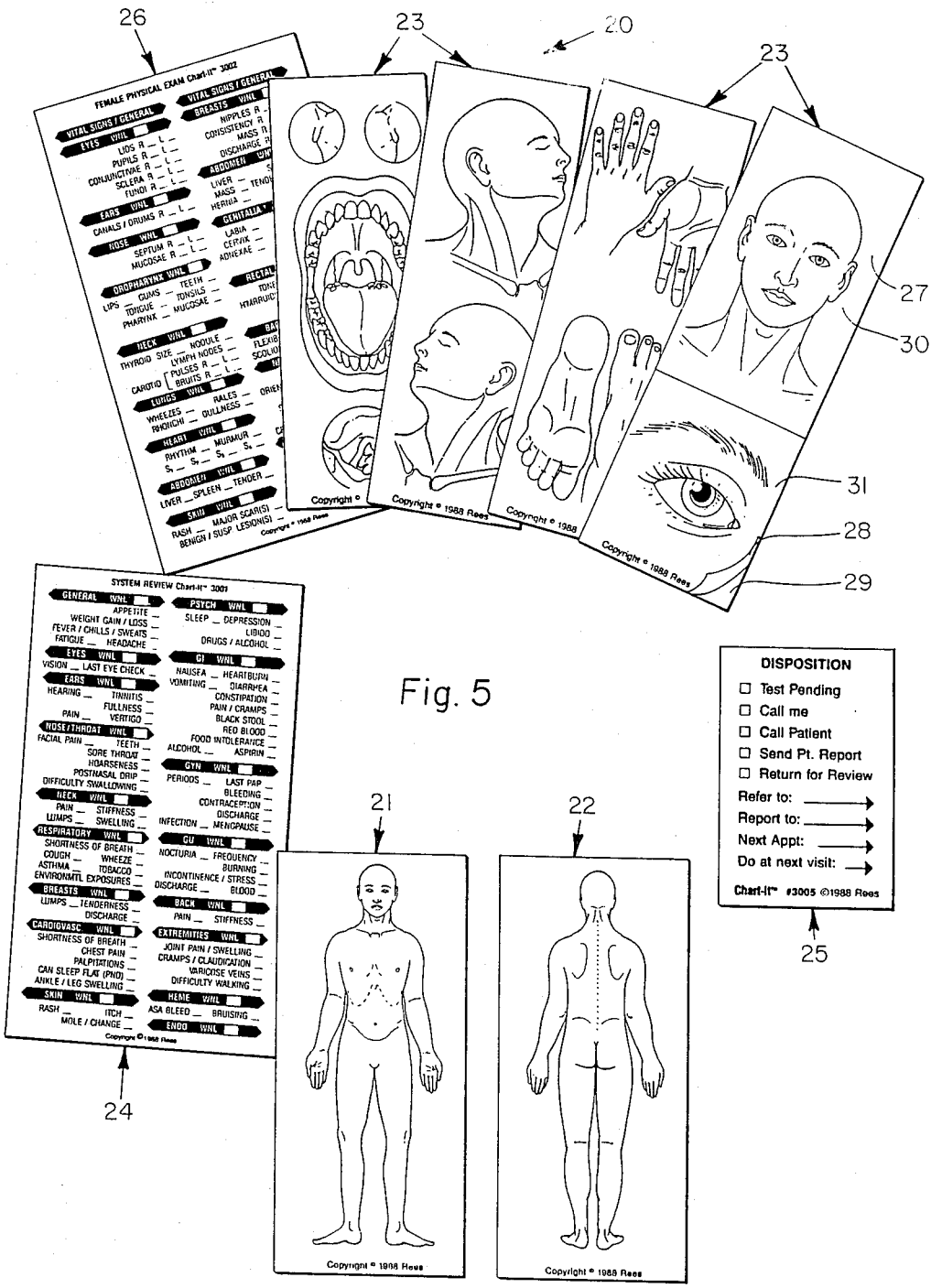
FIG. 5 is a top plan view of representative stickers.

A physician is shown using the dispenser in FIG. 2. During a physical examination, the physician selects those stickers 20 which relate to the examination in question. For example, a sticker 24 (FIG. 5) defines a "System Review" which provides a general outline to the physician for taking a history of the patient and recording his or her symptoms. The physician may then attach the System Review sticker 24 to the progress report 60 and review each of the items listed with the patient to document that the specified areas have been discussed by the patient and the physician. The box "WNL" may be checked when the condition is "within normal limits." The physician may record abnormal findings on the progress report approximately in line with the arrows on the sticker which designate the condition in question. By writing the abnormal findings approximately in line with the designated arrows, the information is organized in a predictable order that facilitates retrieval of information.

Another sticker 26 (FIGS. 5–6) presents a check-list for recording anatomical findings during an examination. This sticker assists the physician in covering each of the designated areas during a standard physical examination and speeds the documentation by allowing the physician to enter a simple check-mark where conditions are normal. FIG. 6 shows how the sticker 26 contains all of the information required in a standard physical examination but in a highly compact and easy-to-use format (compare the prior art narrative 99 on the left). This sticker would also be attached to the progress report.

Also provided are stickers 21 and 22 showing the front and rear of a human body and stickers 23 showing other selected portions of the human anatomy. These stickers can be used by either the patient or physician to mark the exact location, shape and size of a pain, injury, or other abnormality. This provides a permanent record, preferably in the patient s own marking, of what the patient represented to be his or her condition at the time of the examination. For example, as shown in FIG. 2, the patient or physician can mark with pen 62 an X on the front surface 27 of a sticker 21 at the upper left chest to indicate a pain or abnormality. The patient or physician could further indicate by a line eminating from the X the direction in which the pain travels, if applicable. This sticker is then attached to the physician's progress report 60 as a permanent record. Another sticker 20 is shown attached to report 60 with a short narrative to the right of the sticker.

Yet another sticker 25 (FIG. 5) has a checklist and fill-in lines to designate the disposition of the examination, e.g., whether a follow-up telephone call, return visit, or referral is appropriate. This sticker can be both placed on the progress report 60 and given to the patient as a reminder.

Figure 4:
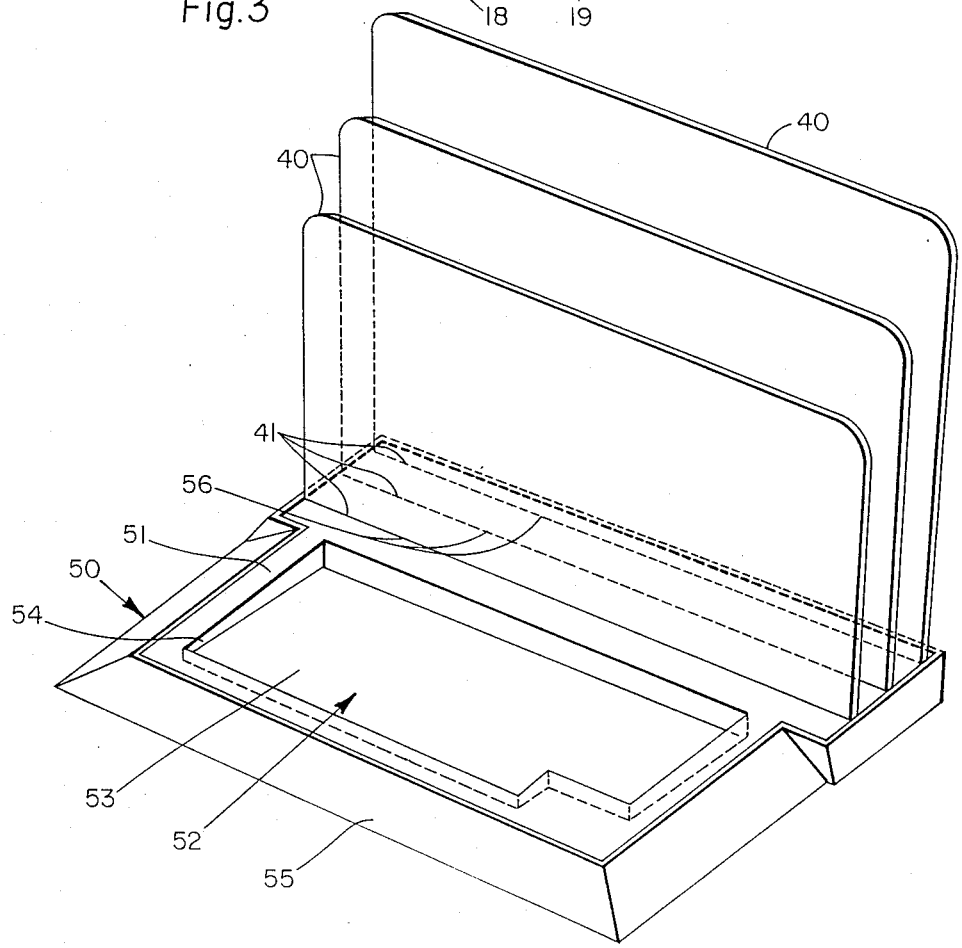
FIG. 4 a top perspective view of the base and report dividers.

As shown in FIG. 4, the base 50 of the kit has an upper wall 51, a peripheral slanted flange 55, a front cavity 52, and three parallel transverse slots 56 in the rear. The front cavity 52 consists of a horizontal bottom wall 53 and vertical sidewalls 54 and is dimensioned to slidably receive a lower peripheral portion of the dispenser 11. The rear slots 56 receive the lower edges 41 of dividers 40, between which progress reports 60 or other papers may be held. The base 50 thus holds the dispenser 11 and compartments for the progress reports adjacent to one another and the composite may be handled as a unit by picking up the base 50 and transporting it to any location. Alternatively, the dispenser may be separated from the base and used alone.

The physical examination kit of this invention thus provides a system for increasing practice efficiency, reducing malpractice exposure, and improving the quality of the medical record. The pre-printed stickers allow the physician to check off normal findings and quickly maintain a record of every body part or condition covered at the examination. The stickers allow the patient or physician to denote the size, location and shape of any abnormal condition or symptom with a minimum of additional narrative. The stickers are attached to the patient report and provide an efficient, accurate and entirely reproducible method of documenting the examination. The dispenser is constructed so that all stickers are in full view. The kit takes up a minimum amount of space on the physician's examination room desk. Alternatively, the dispenser could be mounted on the wall.

The system allows the physician to fully document even the most complex clinical findings within 30 to 90 seconds without acquiring any new skills. Clinical documentation is rapid and precise and information retrieval is greatly facilitated. Abnormal findings are recorded adjacent to that portion of the sticker denoting the system in question. This way, when information is to be retrieved, the reader knows exactly where on the page each body portion examined has been described. The system also includes a disposition sticker which is used at the end of the clinical encounter and provides a rapid method of highlighting the discharge plan.

Examination kits can be developed for different specialties, such as primary care/cardiology (including internal medicine, general practice, and family practice); pediatrics; orthopedic surgery; otolaryngology; obstetrics/gynecology; dermatology; and opthomology. Although a particular group of stickers may be recommended for a given specialty, the physician can select from the universe of stickers so that the unique informational needs of any practice can be satisfied.

The system is efficient because it reduces both the amount of time as well as money that must be spent on medical documentation. The narrative description of normal and abnormal findings can be reduced to a minimum. As a result, the need to dictate notes for later transcription is greatly reduced. This will save many dollars per year. Stenographic services cost anywhere from $150.00 to $400.00 per week, and the average dictated progress note costs approximately $2.30. This compares to the 5–25¢ average cost of a progress note made according to this invention.

The time savings gives the physician more time to focus on the patient in any encounter. The system reduces malpractice exposure by providing improved documentation. The improved documentation is also important for third-party audits such as Medicare.

The system is inexpensive, requires negligable start-up costs, and requires little or no training.

The system reduces malpractice exposure in a number of ways. It increases the ability of the physician to record and retrieve information in a minimum of time. It improves the ability of the physician to communicate with the patient and other providers. It makes the patient chart more legible. It allows physicians to document negatives as well as positives.

A further advantage is that the pre-printed stickers are applied directly to the progress note. No extra pages are inserted into the patient's record. The continuity of the progress note is preserved. Flexibility is preserved because only as much of the pre-printed form is used as the clinical encounter requires.

A further embodiment of this invention is a portable record keeping system to enable the physician to generate complete and accurate records when work is done out of the office, e.g., at a hospital, nursing home, or patient's home. As shown in FIGS. 7–9, the system 70 includes a wallet with internal pockets and a clip for holding a variety of items useful in recording both the physical examination findings and financial data from an out-of-office encounter.

The wallet 71 consists of an outer binding 72 including a front cover 7, rear cover 74, and flexible connecting portion 75. The binding is preferably made of plastic and the wallet is approximately the size of a personal checkbook (see closed wallet in FIG. 8). When opened, the interior of the wallet includes, on the left-hand side 76, a bottom full pocket 77 having a slit opening towards the fold portion 75 of the wallet, a top flap 78 above the bottom pocket, and a clip 79 disposed above the flap. Clip 79 releasably secures the top edges of visitation forms 83 which may be disposed above or below flap 78. On the right-hand side 80 there are provided in a tiered array six smaller pockets 81 each holding stickers 20, and below that, also in a tiered array, three larger pockets 82 holding stickers 24, 26 and an encounter form sticker 84.

As previously noted, a physician's responsibility for patient care does not end at the close of office or clinic hours, and a number of important medical decisions are routinely made either over the telephone or otherwise out of the office without ready access to the patient's permanent record. For example: prescriptions are called into pharmacies; instructions are given with regard to a specific complaint out of the office; medical advice is given over the phone; etc. It is essential that such information become part of the patient's permanent medical record. For this purpose, the encounter form sticker 84 is included in the system 70 on which the encounter may be recorded and the sticker stored in the wallet until such time as it can be permanently affixed to the patient's record. Thus, on the front surface of the encounter form there are provided blank spaces for entering the date, time, caller, patient, complaint, recommendation, prescription, and author. Adhesive is provided on the rear surface of sticker 84 to enable permanent attachment of the form to the patient record when the physician returns to his office.

It is also important for a physician to keep a record of financial data concerning out-of-office visits. Right-hand side of wallet 71 contains a clip 79, top flap 78 and bottom pocket 77 for handling the physician s visitation slips on which such financial data may be recorded. The wallet is designed so that the active visitation slips being used are held in the top flap 78 either with or without the aid of clip 79 so that they can be easily extracted upon demand. Blank visitation slips are stored in the lower pocket 77 until needed. The visitation slip, as shown in FIG. 10, is a $6'' \times 2\frac{5}{8}''$ preprinted form on cardstock that allows the recording of the following essential information: on the front, patient name, location, hospital or unit number, date of visit, classification of visit or consultation (brief, intermediate, complex, extensive) with appropriate billing codes, notes concerning the procedure performed, diagnosis; and on the rear, the referring physician, patient identification information, and insurance and financial information concerning payment. For example, a physician making hospital rounds may wish to order the visitation slips within flap 78 by floor number. With the visitation slips held only by the flap 78 and clip 79, the physician can introduce new slips or relocate slips when new patients are added or when the location of a patient changes. These actions can be taken without disturbing the order of the entire file.

The additional stickers 20 held in the pockets 81, 82 on the right hand side of the wallet are intended to be used in the same manner as the stickers described in the previous embodiment, wherein selected stickers are chosen by the physician which relate to a specific examination and the stickers are attached to the patient report. The wallet pockets are designed, similar to the dispenser 11, to provide an array of stickers wherein an identifying designation on a sticker in each pocket is readily viewable by the physician while the stickers are held in the pockets.

The wallet shown is designed to store ten of each of the following: medical encounter form sticker 84; physical examination sticker 26, review of system sticker 24; and six individual anatomical illustrations (ten of each) as selected by the physician. The wallet also stores 50 of visitation slips 83. Of course, the physician may wish to alter the types and quantities of the various components of the system as dictated by the needs of the individual practice.

Having described certain preferred embodiments of the invention in detail, those skilled in the art will appreciate that numerous modifications may be made thereof without departing from the spirit of the invention. Therefore it is not intended that the scope of the invention be limited to specific embodiments illustrated and described but rather it is intended that the scope of the invention be determined by the appended claims and their equivalents.

What is claimed is:

1. A medical recording system comprising:
   a dispenser having an array of compartments;
   a plurality of pre-printed recording stickers having on one surface one of several anatomical dsignations, including depictions of anatomical features, and on the opposing surface an adhesive means;
   said array of compartments being sized and configured to hold an array of said stickers, wherein a physician can view the array of stickers in said dispenser during a physical examination and selectively remove those stickers which relate to the examination, and attach those stickers to a report to document the findings of the physical examination.

2. The system of claim 1, wherein the one surface of the stickers having an anatomical designation is made of a material that permits writing thereon.

3. The system of claim 1, wherein the anatomical designations include a list of body portions to be examined during a physical examination.

4. The system of claim 1, wherein the anatomical designations include a check-lists of body portions or symptoms to be examined during a physical examination.

5. The system of claim 1, wherein the compartments facilitate visual identification of the stickers held in the compartments.

6. The system of claim 1, wherein the dispenser is a desk-top dispenser.

7. The system of claim 1, wherein the dispenser is a wallet.

8. The system of claim 7, wherein the system further includes a sticker for recording an out-of-office encounter.

9. The system of claim 7, wherein the wallet includes means for holding forms including pocket means and clip means.

10. A method for recording the findings of a physical examination comprising:
    providing an array of pre-printed recording stickers having on one surface an anatomical designation and on the opposing surface an adhesive means, said anatomical designations including graphical representations of various body portions;
    selecting from the array those stickers which relate to a physical examination;
    marking on said graphical representations the location of any abnormal occurrences; and
    attaching those stickers to a progress report for documenting the findings of the physical examination.

11. The method of claim 10, wherein the patient marks on the body portion the location of an abnormal occurrence.

12. A medical recording system comprising a plurality of stickers, each sticker having on one side one of several pre-printed formats, including depictions of anatomical features, and on the opposing surface an adhesive means, wherein during an encounter with a patient, a physician can selectively attach those stickers, which relate to the encounter, to a report, such that the physician may quickly, efficiently and comprehensively document the encounter.

13. A medical recording system according to claim 12, wherein some of the formats represent a list of body portions to be examined during a physical examination.

14. A medical recording system according to claim 13, wherein some of the formats permit entry of administrative and financial information.

15. A system for recording an examination of a patient by a physician comprising:
    a plurality of checklist stickers, each checklist sticker having on one side an adhesive means and on the opposing side one of several pre-printed checklists, each checklist having few enough items so that the physician need include in the report only those items that are pertinent to the examination, and each checklist being detailed enough so that the physician can thoroughly document normal findings of the examination by making marks on the checklist sticker.

16. A system according to claim 15, further including:
    a report sheet, to which the checklist sticker can be attached, if the checklist sticker is pertinent to the examination, and on which abnormal conditions can be noted next to the pertinent checklist sticker.

17. A system according to claim 15, further comprising:
    a plurality of anatomy stickers, each anatomy sticker including a material that permits writing thereon, and each anatomy sticker having on one side an adhesive means and on the opposing side one of several pre-printed depictions of anatomical features.

* * * * *